United States Patent [19]

Frey et al.

[11] Patent Number: 4,917,704
[45] Date of Patent: Apr. 17, 1990

[54] INTERVERTEBRAL PROSTHESIS

[75] Inventors: Otto Frey, Winterthur; Rudolf Koch, Berlingen, both of Switzerland

[73] Assignee: Sulzer Brothers Limited, Winterthur, Switzerland

[21] Appl. No.: 204,020

[22] Filed: Jun. 8, 1988

[30] Foreign Application Priority Data

Jul. 9, 1987 [CH] Switzerland ............... 2606/87-1

[51] Int. Cl.⁴ ............................................. A61F 2/44
[52] U.S. Cl. ........................................ 623/17; 128/69; 606/61
[58] Field of Search ............... 623/16, 18, 17, 20; 305/35 EB, 13; 152/209 R; 360/32 R; 128/69, 92 YM, 92 YP

[56] References Cited

U.S. PATENT DOCUMENTS

| | | | |
|---|---|---|---|
| 2,677,369 | 5/1954 | Knowles | 623/16 X |
| 3,867,728 | 2/1975 | Stubstad . | |
| 4,034,418 | 7/1977 | Jackson et al. | 623/20 |
| 4,064,567 | 12/1977 | Burstein et al. | 623/20 X |
| 4,108,229 | 8/1978 | Herman | 305/13 X |
| 4,568,294 | 2/1986 | Owsen | 305/35 EB |
| 4,599,086 | 7/1986 | Doty | 623/17 |
| 4,611,581 | 9/1986 | Steffee | 128/69 |
| 4,714,469 | 12/1987 | Kenna | 623/17 |

FOREIGN PATENT DOCUMENTS

| | | |
|---|---|---|
| 0042271 | 12/1981 | European Pat. Off. ............. 623/17 |
| 0179695 | 4/1986 | European Pat. Off. . |
| 2263842 | 7/1974 | Fed. Rep. of Germany . |
| 2365873 | 8/1976 | Fed. Rep. of Germany . |
| 2372622 | 6/1978 | France . |
| 1107854 | 8/1984 | U.S.S.R. ............................ 623/17 |

Primary Examiner—V. Millin
Assistant Examiner—David J. Bender
Attorney, Agent, or Firm—Kenyon & Kenyon

[57] ABSTRACT

The intervertebral prosthesis provides a replacement for a damaged disk. The prosthesis is formed as a solid body of kidney-shape and is provided with a metal mesh covering for the ingrowth of tissue. Raised parts are formed on the opposite surfaces of the kidney-shaped body impart lateral stability when in situ.

14 Claims, 1 Drawing Sheet

INTERVERTEBRAL PROSTHESIS

This invention relates to an intervertebral prosthesis. More particularly, this invention relates to an intervertebral prosthesis for an arthrodesis.

As is known, for an arthrodesis of two lumbar vertebrae relative to each other, two different approaches have been customary. In one approach, bone splinters have been removed from another part of the body, for example, from the pelvis or the shin, and placed as a partial replacement of the damaged intervertebral disk between the two vertebrae from the ventral direction and secured with bone screws. However, it has been shown that securement of the two adjacent vertebrae is insufficient and does not have the requisite stability, especially shortly after implantation when the bone tissue of the Vertebrae has not yet become intergrown with the bone splinters.

In the other approach, two adjacent vertebrae have been secured relative to each other by cross plates which are firmly connected with the two vertebrae from the dorsal direction, for example by means of screws. However, experience has shown that the cross plates which are arranged relatively far from the intervertebral disks effect only an insufficient securement of the vertebrae in the dorsal region of the vertebrae, particularly in the case of a greater intervertebral disk damage or in the case of a complete replacement of an intervertebral disk. Also, the plates tend toward instabilities in the reciprocable stiffening of the vertebrae.

French Patent 2372622 describes an intervertebral prosthesis which is formed of a disk and which is provided with weld-like raised parts in the form of spherical segments on opposite sides. Such a disk is to be placed between a pair of vertebrae with the spherical segments placed in hollow spherical-shaped depressions of the vertebrae. In this case, the disk is stiff and non-deformable while the raised parts are elastic. However, an arthrodesis of the two vertebrae is not possible with such a construction.

Various types of intervertebral prosthesis have also been known for implantation within a spinal column. For example, German OS 2365873 describes a skeletal type prosthesis which can be implanted in place of a vertebrae and secured in situ by means of screws to adjacent vertebrae. German 0S 263842 describes a composite disk like structure which is to be implanted between a pair of vertebrae to replace a damaged disk. HoWeVer, the stability of such a prosthesis cannot be ensured since no means is provided for a primary fixation of the prosthesis in place. Published European Patent Application 179695 describes a prosthesis which is intended to replace a damaged disk and which is constructed of a peripheral ring with a multi-apertured insert. However, such a prosthesis is relatively cumbersome to use and does not provide for a primary fixation of the prosthesis in situ. U.S. Pat. No. 3,867,728 describes a prosthesis for spinal repair Which is made of a core element of elastic polymer and an outer covering of porelike material to provide for tissue ingrowth. However, the securement of such a prosthesis in place cannot be readily obtained and the prosthesis does not have the required stability for primary fixation.

Accordingly, it is an object of the invention to provide an intervertebrae prosthesis which can be implanted and secured at relative low operative expense.

It is another object of the invention to ensure a firm and stable stiffening of two vertebrae when using an intervertebral disk replacement.

Briefly, the invention provides an intervertebral prosthesis comprised of a disk-like body which can be slid between two vertebrae from the ventral direction to function as a disk replacement. In addition, the disk-like body is provided with weld-like raised parts on opposite surfaces to enhance lateral stability of the body in situ.

The prosthesis is distinguished by great simplicity since the prosthesis is formed solely of a disk-like body for fitting between a pair Of vertebrae. The weld-like raised parts which are preferably of a cross section having a cylindrical segment shape form an acute angle with each other and are placed from the ventral direction into surgically prepared bores of the vertebral bodies which are adapted to the raised parts. These raised parts thus ensure lateral stabilitY of the arthrodesis as well as primary securement. Furthermore, it is advantageous if the angle formed by the raised parts on a given surface is 90°.

In Order to adapt the prosthesis to the anatomical conditions, the prosthesis body may be kidney-shaped and/or may have a thickness which tapers conically from ventral to dorsal.

The prosthesis body may be of a synthetic material, for example, polyethylene having the specifications customary for implants. In addition, the surfaces of such a synthetic material body may be covered with a metal mesh, for example, a multi-layered wire mesh of titanium or a titanium alloy in order to support tissue ingrowth and thereby ensure a long term securement.

Alternatively, the prosthesis body may consist of titanium or a titanium alloy. In this case also, the surfaces of the body may be provided with a structure which supports tissue ingrowth and which may also be formed of a wire mesh secured to the disk body by spot welding.

These and other objects and advantages of the invention will become more apparent from the following detailed description taken in conjunction with the accompanying drawings wherein.

Figure 1:
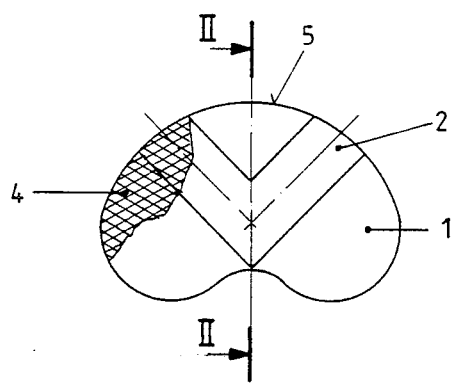
FIG. 1 illustrates a plan view of a prosthesis constructed in accordance with the invention.

Referring to FIG. 1, the intervertebral prosthesis is comprised of a disk-like body 1 for fitting between a pair of vertebrae and is provided with a pair of weld-like raised parts 2 on each of two opposite surfaces to enhance lateral stability of the body 1 in situ. As indicated, the raised parts 2 define a chevron rib and are disposed on axes which define an angle of 90°. As seen in FIG. 1, the rib defined by the raised parts 2 is directed from ventral to dorsal.

Figure 2:
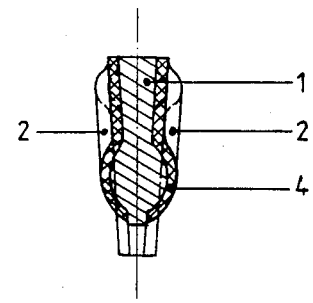
FIG. 2 illustrates a cross-sectional view taken on line II—II of FIG. 1.

The disk 1 is of kidney or bean-shape which is curved convex ventrally and concave dorsally. In addition, the body 1 has a thickness which decreases from ventral to dorsal as indicated in FIG. 2.

Figure 3:
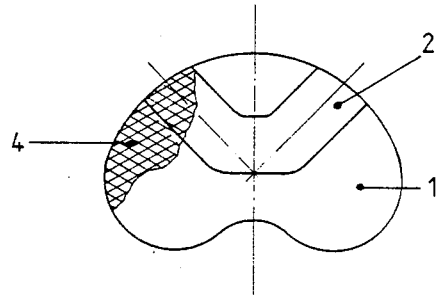
FIG. 3 illustrates a plan view of a modified prosthesis in accordance with the invention.
Figure 4:
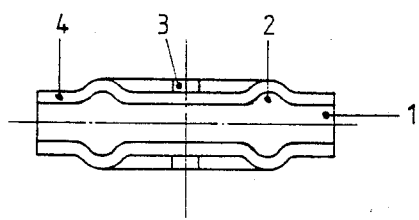
FIG. 4 illustrates a view of the prosthesis of FIG. 3 from dorsal to ventral.

The raised parts 2 each extend from the ventral edge 5 to the dorsal edge. However, as indicated in FIG. 3, the parts 2 may terminate in the region where the axes of the parts 2 intersect. In this case, the parts 2 are connected by a bridge-like web 3 (see FIG. 4).

The entire prosthesis including the body 1 and the parts 2 are covered with a multi-layered wire mesh 4, for example of titanium. Where the body 1 is made of a synthetic material such as polyethylene, at least one layer of the mesh 4 may be embedded in the body 1. In known manner, the mesh 4 serves to support tissue in growing onto and into the mesh.

Figure 5:
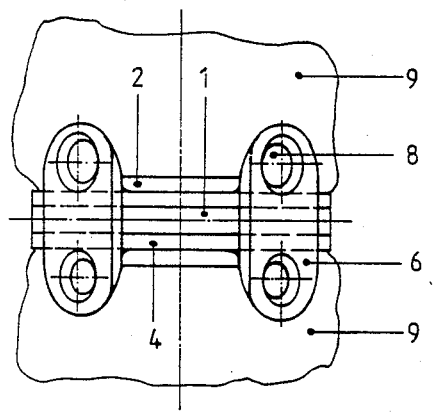
FIG. 5 illustrates a view of a prosthesis in situ between two vertebrae.

Referring to FIG. 5, in order to improve a primary securement of the prosthesis prior to ingrowth of bone tissue, the ventral edge 5 of the body 1 is covered by a pair of fishplates 6. As indicated, the fishplates 6 only partially cover the ventral edge. In addition, each plate 6 is provided with a pair of openings 8 for the passage of bone screws into the adjacent vertebrae 9. These openings 8 are formed as part of a spherical bowl in order to facilitate alignment of the screws (not shown) in any direction.

Figure 6:
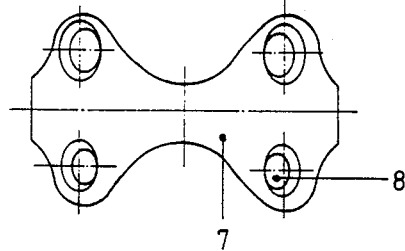
FIG. 6 illustrates a ventral view of a modified prosthesis in accordance with the invention.

Referring to FIG. 6, the prosthesis may also be provided with an integral fishplate arrangement 7 which covers the ventral edge 5, for example, as described in copending patent application Ser. No. 07/203,950, filed June 8, 1988. In this case, the fishplate arrangement 7 has pairs of openings 8 as above.

During implantation of the prosthesis body, for example, from ventral to dorsal, the body is slightly compressed by the vertebrae 9. Thereafter, the fishplates 6 or fishplate arrangement 7 can be secured to the Vertebrae 9 by means of bone screws to effect primary fixation.

The invention thus provides a prosthesis which can be used as an intervertebral disk replacement which ensures a stable stiffening (arthrodesis) of two vertebrae relative to each other. In addition, the raised parts of the prosthesis body which are placed into surgically prepared bores in the vertebrae ensure a primary securement and an increased lateral stability of the prosthesis.

What is claimed is:

1. An intervertebral prosthesis for an arthrodesis comprising a disk-like body for fitting between a pair of vertebrae, said body having weld-like raised parts disposed on opposite surfaces thereof dimensioned to enhance lateral stability of said body in situ, each said raised part on said body having a cross-section of cylindrical segment shape and forming an acute angle with a second raised part on a respective surface of said body.

2. An intervertebral prosthesis as set forth in claim 1 wherein said angle is equal to 90°.

3. An intervertebral prosthesis as set forth in claim 1 wherein said raised parts on each surface of said body define a chevron shaped rib directed from ventral to dorsal.

4. An intervertebral prosthesis as set forth in claim 1 wherein said body is kidney-shaped.

5. An intervertebral prosthesis as set forth in claim 1 wherein said body tapers conically from ventral to dorsal.

6. An intervertebral prosthesis as set forth in claim 1 wherein said body is made of synthetic material and which further comprises a metal wire mesh on said opposite surfaces for an ingrowth of tissue.

7. An intervertebral prosthesis as set forth in claim 1 wherein said body is made of a metal selected from the group consisting of titanium and titanium alloy.

8. An intervertebral prosthesis for an arthrodesis comprising a kidney-shaped disk-like body for fitting between a pair of vertebrae, said body having a raised chevron-shaped rib disposed on opposite surfaces thereof to enhance lateral stability of said body in situ, each said rib projecting from a respective surface along the length thereof.

9. An intervertebral prosthesis as set forth in claim 8 wherein each rib has a cross-section of cylindrical segment shape.

10. An intervertebral prosthesis as set forth in claim 8 wherein each chevron shaped rib is directed from ventral to dorsal.

11. An intervertebral prosthesis as set forth in claim 8 wherein said body is made of synthetic material and which further comprises a metal wire mesh on said opposite surfaces for an ingrowth of tissue.

12. An intervertebral prosthesis for an arthrodesis comprising a kidney-shaped disk-like body for fitting between a pair of vertebrae, said body having raised parts disposed on opposite surfaces with each part projecting from a respective surface along the length thereof, each part extending from a ventral edge towards a dorsal edge along an axis intersecting with a ventral-to-dorsal plane of said body and with an axis of another of said parts to enhance lateral stability of said body in situ.

13. An intervertebral prosthesis as set forth in claim 12 wherein said parts on each surface define a chevron-shaped rib.

14. An intervertebral prosthesis as set forth in claim 12 wherein said parts on each surface terminate in a region where said axes thereof intersect and a bridge-like web on each surface connects said parts thereat.

* * * * *

UNITED STATES PATENT AND TRADEMARK OFFICE
CERTIFICATE OF CORRECTION

PATENT NO. : 4,917,704

DATED : April 17, 1990

INVENTOR(S) : OTTO FREY, et al

It is certified that error appears in the above-identified patent and that said Letters Patent is hereby corrected as shown below:

```
Column 1, line 18  "Vertebrae" should be -vertebrae-
Column 1, line 48  "263842" should be -2263842-
Column 1, line 51  "Ho We Ver" should -However-
Column 1, line 60  "Which" should be -which-
Column 2, line 12  "Of" should be -of-
```

Signed and Sealed this

Seventeenth Day of September, 1991

Attest:

HARRY F. MANBECK, JR.

Attesting Officer

Commissioner of Patents and Trademarks